United States Patent [19]
Mitchell et al.

[11] 4,342,390
[45] Aug. 3, 1982

[54] APPARATUS FOR HOLDING AND PROTECTING STERILIZABLE INSTRUMENTS

[76] Inventors: James G. Mitchell; Winalee G. Mitchell, both of 110 Secor Woods La., Perrysburg, Ohio 43551

[21] Appl. No.: 114,167

[22] Filed: Jan. 22, 1980

[51] Int. Cl.³ .............................................. B65D 83/10
[52] U.S. Cl. ................... 206/363; 206/372; 206/459; 206/523
[58] Field of Search ............... 206/363, 455, 372, 373, 206/489, 523

[56] References Cited

U.S. PATENT DOCUMENTS

| 847,254 | 3/1907 | Jackson | 206/373 |
| 1,094,009 | 4/1914 | Parkhurst | 206/373 |
| 1,679,101 | 7/1928 | Sternthal | 206/372 |
| 2,923,404 | 2/1960 | Adell | 206/459 |
| 3,685,720 | 8/1972 | Brady | 206/459 |
| 3,749,233 | 7/1973 | Mc Cormick, Jr. | 206/373 |
| 3,861,521 | 1/1975 | Burtz | 206/363 |
| 4,142,632 | 3/1979 | Sandel | 206/363 |

Primary Examiner—Joseph Man-Fu Moy
Attorney, Agent, or Firm—Pollock, Vande Sande & Priddy

[57] ABSTRACT

An improved holder and protector (10) for sterilizable instruments is disclosed which comprises two layers (12) of heat fusible, reticulated foam material joined to define a plurality of open-ended pockets (18) for receiving instruments and a cover flap (22) for folding over the instruments and pockets to protect them. A strip (20) of the layers below the pockets is fused to provide a smooth surface on which indicia of the contents of the pockets may be provided, as by manual printing.

15 Claims, 3 Drawing Figures

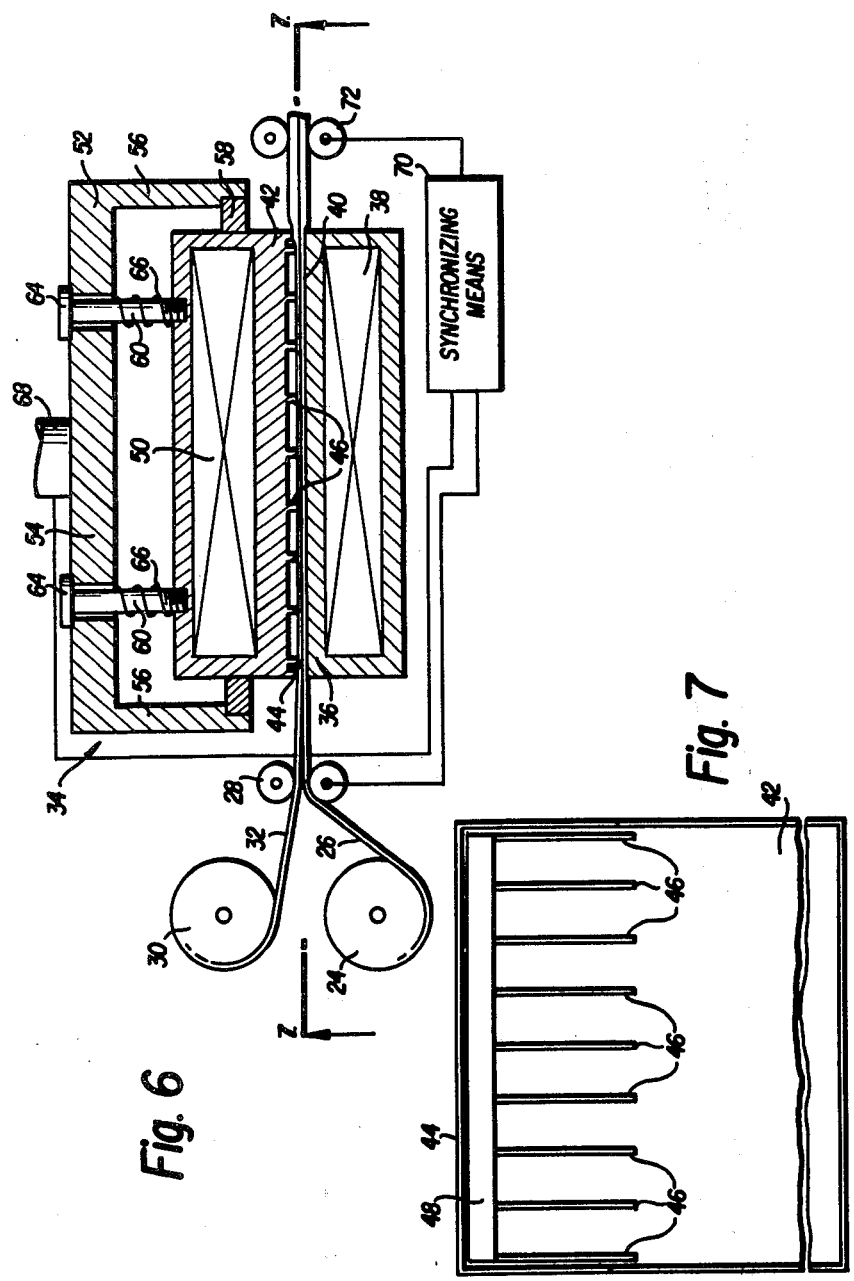

APPARATUS FOR HOLDING AND PROTECTING STERILIZABLE INSTRUMENTS

DESCRIPTION

1. Technical Field

The present invention concerns special purpose receptacles or packages. Particularly, the invention comprises improvements to packages of the type used to hold and protect medical or surgical instruments both initially during sterilization and subsequently during various medical and surgical procedures.

2. Background Art

Various types of packaging techniques have been used over the years to organize and protect surgical instruments during and following sterilization. Typically, the instruments for a particular surgical procedure have been inserted into some type of package prior to sterilization. Following sterilization, the package may be retained in storage until the instruments are needed, at which time the package is opened. Recently, reticulated foam holders for instruments have come into use which not only protect the instruments during sterilization and storage, but also facilitate handling the instruments during surgical procedures. U.S. Pat. No. 4,142,632 issued to Sandel discloses such a holder or protector.

Although prior art holders for instruments have proven satisfactory in many applications, difficulties have been experienced with them. Where pockets are provided for the instruments, so much of the instrument may be hidden that the user cannot conveniently determine the identity of each instrument when the sterile package is opened. The Sandel patent discloses a solution to this difficulty in that a coarse or large pore reticulated foam is used for portions of the pockets, so that the tips of the instruments can be seen through the foam. This arrangement has some advantages but the coarse foam may snag on some instruments. However, the use of finer pore foam to reduce snagging makes it difficult to identify the instrument since it is no longer visible through the foam.

Disclosure of the Invention

A primary object of the present invention is to provide an improved apparatus for holding and protecting sterilizable instruments during actual sterilization and subsequent surgical or other procedures.

A further object is to provide such an apparatus which comprises separate pockets for each instrument, plus means for readily providing indicia of the types of instruments located in the pockets.

Yet another object of the invention is to provide such an apparatus in which fine pore reticulated foam is used to form the instrument receiving pockets and a portion of the foam near each pocket is fused to provide a relatively smooth writing surface for receiving identifying indicia for the instruments.

Those skilled in the art may perceive other desirable objects and advantages inherently achieved by the present invention. Nonetheless, the scope of the invention is to be limited only by the appended claims. In a preferred embodiment of the invention, the apparatus for holding and protecting sterilizable instruments comprises a first layer of sterilizable material and a second layer of sterilizable material overlying a portion of the first layer. A plurality of open-end pockets are defined between the two layers by essentially parallel seams joining the layers. Near each of the pockets, the surface of at least one of the layers is prepared for receiving indicia of the content of the adjacent pockets.

Preferably, the two layers of the apparatus are made from fine pore reticulated polyurethane foam material, having a pore size of about 80 pores per lineal inch. Such material is readily available and is sterilizable by steam or ethylene oxide sterilizing gas. Moreover, it fuses to itself or an adjacent layer upon application of heat and pressure, so that strong seams can be formed. By applying heat to a relatively wide strip of material on or adjacent to the pockets, a smooth, fused surface is obtained which is suitable for marking with a conventional writing instrument such as ballpoint pens, felt tip markers and the like. The pockets of the apparatus are provided at one end of the first layer of material so that the opposite end may be folded over the instruments following their insertion into the pockets.

BRIEF DESCRIPTION OF THE DRAWINGS

FIG. 6 shows a schematic sectional view of an apparatus for making the invention.

FIG. 7 shows a view taken on line 7—7 of FIG. 6, illustrating a plan view of the heat sealing dies used to make the invention.

BEST MODE FOR CARRYING OUT THE INVENTION

Figure 1:
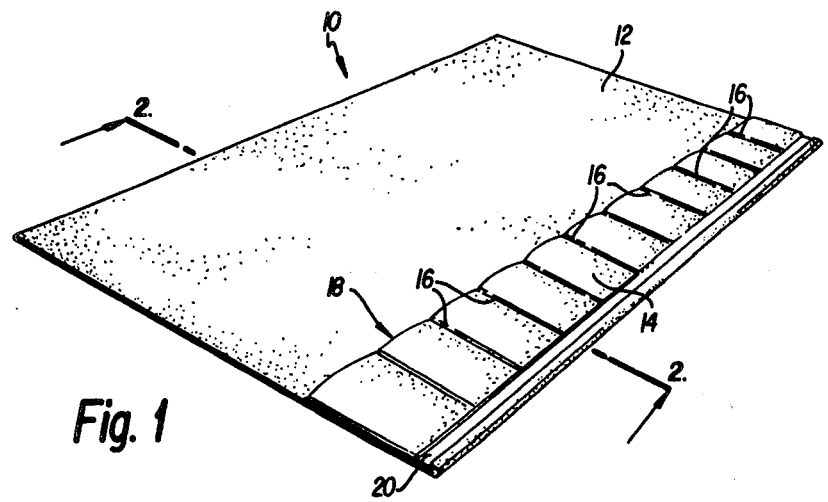
FIG. 1 shows a perspective view of an instrument organizer and holder according to the invention.

The invention will be described with reference to the drawings, in which like reference numerals identify like elements of structure in each of the several Figures.

Figure 2:
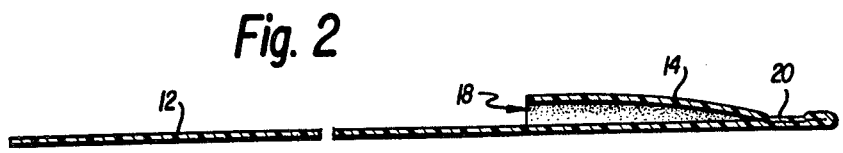
FIG. 2 shows a sectional view taken on line 2—2 of FIG. 1.
Figure 3:
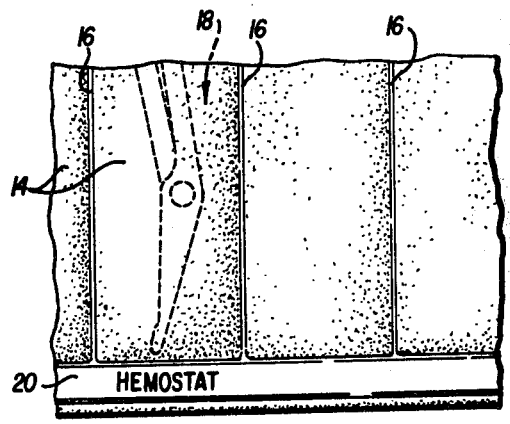
FIG. 3 shows a fragmentary view of the invention, indicating the surface for receiving identifying indicia.

Referring to FIGS. 1 to 3, the instrument organizer and protector 10 according to the invention is seen to comprise a first rectangular layer 12 of a suitable sterilizable material such as fine pore polyurethane foam. A second layer 14 overlies layer 12 along one edge, as illustrated, though layer 14 also may be moved more toward the center of layer 12, as desired. Layer 14 may be a separate strip of material, as illustrated, or may be an extension of layer 12 folded back to form the two layers required. A plurality of thermally fused, essentially parallel side seams 16 are provided to attach layer 14 to layer 12 and thus to define the side seams of a plurality of pockets 18. Seams 16 could also be sewn or glued; however, fused seams are preferred. The seams are long enough and layer 14 is wide enough to ensure that instruments will be secure in the pockets yet readily accessible when needed.

The bottoms of pockets 18 are formed by a wide seam or fused area 20 extending across the width of both layers 12 and 14 and fusing them together at the bottom of seams 16. Seam 20 preferably is formed by thermally fusing a laterally extending portion of both of layers 12 and 14 approximately three-quarters of an inch in width. The result is a smooth, relatively non-porous surface which is suitable for receiving indicia of the contents of the adjacent pockets, as shown for example in FIG. 3. Such a fused portion could also be provided in layer 12 at a location above the mouths of pockets 18 or at a greater distance below the pockets, as desired. In addition, layer 12 or 14 could be provided with a fused area for receiving indicia before the two layers are joined.

Figure 4:
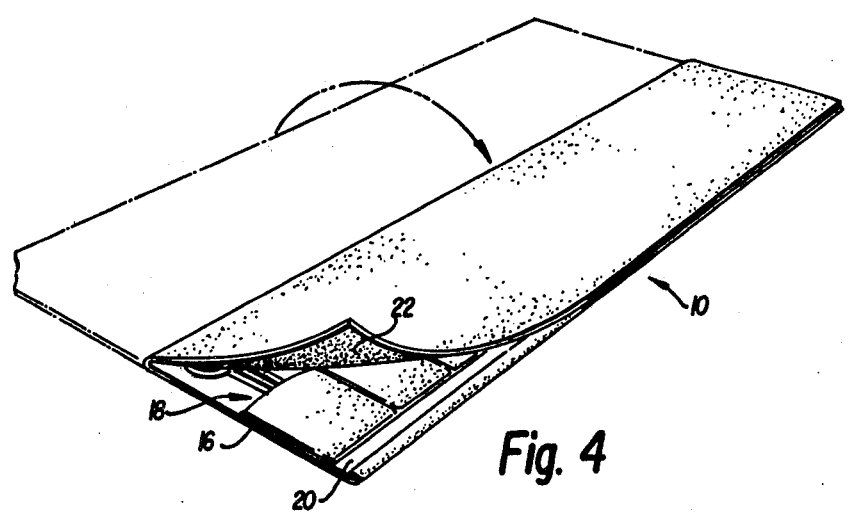
FIG. 4 shows a perspective view of an apparatus according to the invention with its protective flap folded into place above its pockets and their instruments.
Figure 5:
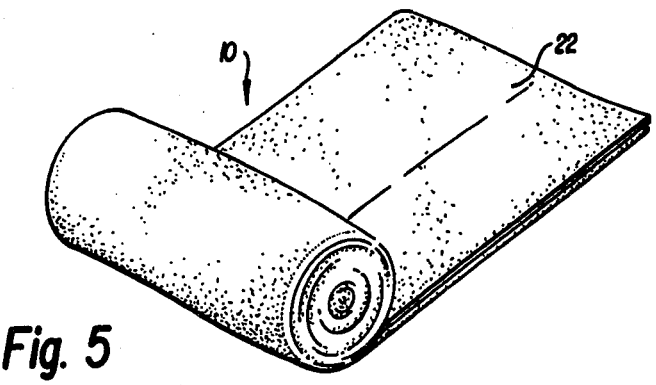
FIG. 5 shows a perspective view of the apparatus of FIG. 4, partially rolled up for further handling.

Once instruments have been placed in pockets 18, appropriate indicia are marked on layer 20. The top portion of layer 12 is folded over to form a flap 22 which further protects the instrument, as shown in FIG. 4. The loaded organizer and protector may then be rolled as shown in FIG. 5 for further processing. When sterilization is to be done, one or more additional wrappings may be placed around the loaded organizer in accordance with known practices. When the instruments are to be used, the additional wrappings are removed at the appropriate time; the organizer is unrolled; and the instruments are readily accessible with the indicia on seam 20 clearly in view to facilitate selection of the correct instrument.

In one actual product embodying the invention, layer 12 was a rectangle approximately 17 inches long and 16 inches wide, made from approximately one-eighth inch thick, fine pore foam. Layer 14 was approximately 5 inches long and 16 inches wide, made from the same material. Seams 16 were four inches long; seam 20 was three-quarters of an inch wide; and each pocket 18 was approximately one and one-half inches wide.

FIGS. 6 and 7 illustrate schematically an apparatus for manufacturing the instrument organizer and protector shown in FIGS. 1 to 5. A roll 24 of polyurethane foam sheet having a width somewhat greater than the desired width of layer 12 dispenses a band 26 of material which is fed between drive rollers 28. A second roll 30 of polyurethane foam sheeting having a width somewhat greater than the desired width of layer 14 dispenses a band of material 32 which also is fed between drive rollers 28 with one edge of band 32 preferably aligned with one edge of band 26. Or, as indicated previously, band 26 could be made of still greater width and folded back on itself to form layer 14, using a folding guide not illustrated. After leaving rollers 28, bands 26 and 32 are drawn in superimposed relationship into a forming and heat sealing die press 34, where seams 16 and 20 are formed and layers 12 and 14 are cut from bands 26 and 32 to form the completed product.

Band 32 passes over a lower, stationary platen 36 having a heater 38, such as one or more induction heaters, located beneath its flat upper surface 40. Band 26 passes beneath an upper, movable heat sealing die 42 having a downwardly projecting perimetral die face 44; a plurality of parallel, downwardly projecting side seam forming die faces 46; and a laterally extending, downwardly projecting bottom seam forming die face 48. See FIG. 7. Die faces 44, 46 and 48 also are heated by a heater 50, such as an induction heater, and preferably are made from tool steel to minimize wear and distortion.

Surrounding heat sealing die 42 is shearing cutter assembly 52 which comprises an upper wall or base 54 from which depend side walls 56, having hardened cutting inserts 58 at their lower ends which conform to the perimetral configuration of die face 44 and platen 36. Shearing cutter 52 functions to separate completed instrument organizers from bands 26 and 32. Legs 60 having flattened heads 64 are mounted in bores in base 54 and attached at their lower ends to upper heat sealing die 42. Springs 66 bias upper heat sealing die 42 away from base 54 and are chosen to provide sufficient compressive force to press die faces 46 and 48 sufficiently close to upper surface 40 to promote the formation of thermally fused seams 16 and 20. An actuating shaft 68 is attached to the upper surface of base 54, through which pressure is applied to close the heat sealing dies.

A synchronizing mechanism 70, of mechanical or other type, programs the sequence of operations of infeed rollers 28, heat sealing die press 34 and outfeed rollers 72. These objectives may easily be attained through the use of electric rotary switch timer clocks or electronic sequence timers, hydraulic and/or pneumatic pumps, solenoid valves, limit switches and related control apparatus with which those skilled in the art are familiar. Thus, mechanism 70 has been shown only schematically.

Perimetral die face 44 terminates in a plane from 0.010 to 0.015 inch above the lower faces of die faces 46, 48. This relief provides an expanded clearance to upper surface 40, thereby minimizing fusing of the edges of layer 12 while still providing a slight sear of the material, which improves edge appearance and is thought to contribute somewhat to strength. The softening of material between die face 44 and surface 40 also permits shear cutter 52 to cut each completed instrument organizer more easily from the surrounding material.

As force is applied to shaft 68 when bands 26 and 32 have stopped, heated die faces 46 and 48 eventually compress bands 26 and 32 to form seams 16 and 20. Simultaneously, shear cutter 52 moves downward to cut the completed product from the bands, after which the die press opens and rollers 28, 72 deliver fresh material. The dies remain closed for only a short time, on the order of a fraction of a second; and shear cutter 52 may complete its motion either before, as, or after die faces 46 and 48 reach their positions for forming seams 16 and 20.

Industrial Applicability

The apparatus according to the invention is particularly useful for organizing, protecting and storing surgical instruments; however, it may also be used for packaging instruments or tools intended for other purposes.

Having described our invention in sufficient detail to enable those skilled in the art to make and use it, we claim:

1. An improved apparatus for holding and protecting sterilizable instruments, comprising:
 a first layer of sterilizable material;
 a second layer of sterilizable material overlying a portion of said first layer and being made from a thermally fusible foam material;
 a plurality of seams joining said layers and defining a plurality of open-end pockets between said layers; and
 means adjacent said pocket, said means comprising a portion of said second layer of foam material in which portion the foam is fused to provide an exterior writing surface for marking with a conventional writing instrument.

2. Apparatus according to claim 1, wherein both said layers are made from thermally fusible material and said seams are thermally fused.

3. Apparatus according to claim 1, wherein both said layers are made from thermally fusible material and said means for receiving indicia comprises a portion of both said layers fused together to provide said exterior writing surface.

4. Apparatus according to claim 1, wherein both said layers are made from thermally fusible foam material.

5. Apparatus according to claim 1, wherein both said layers are made from thermally fusible foam material and said seams are thermally fused.

6. Apparatus according to claim 1, wherein said first layer extends substantially beyond the open ends of said pockets, whereby said first layer may be folded over said second layer and said pockets.

7. Apparatus according to claim 1, wherein both said layers are made from thermally fusible foam material and said means for receiving indicia comprises a portion of said layers fused together to provide an exterior writing surface.

8. Apparatus according to claim 7, wherein said pockets open in one direction and said means for receiving indicia are located adjacent to the opposite ends of said pockets.

9. Apparatus according to claim 7, wherein said first layer extends substantially beyond the open ends of said pockets, whereby said first layer may be folded over said second layer and said pockets.

10. Apparatus according to claim 1, wherein said first layer extends substantially beyond the open ends of said pockets, whereby said first layer may be folded over said second layer and said pockets.

11. Apparatus according to claim 1, wherein both said layers are thermally fusible foam material; said seams are thermally fused; and said means for receiving indicia comprises a portion of said layers fused together to provide an exterior writing surface.

12. Apparatus according to claim 11, wherein said pockets open in one direction and said means for receiving indicia are located adjacent to the opposite ends of said pockets.

13. Apparatus according to claim 11, wherein said first layer extends substantially beyond the open ends of said pockets, whereby said first layer may be folded over said second layer and said pockets.

14. Apparatus according to claim 1, wherein said pockets open in one direction and said means for receiving indicia are located adjacent to the opposite ends of said pockets.

15. Apparatus according to claim 1, wherein said first layer extends substantially beyond the open ends of said pockets, whereby said first layer may be folded over said second layer and said pockets.

* * * * *